United States Patent
Huys et al.

(10) Patent No.: US 9,551,698 B2
(45) Date of Patent: Jan. 24, 2017

(54) MICRONEEDLE

(75) Inventors: Roeland Huys, Wilsele (BE); Wolfgang Eberle, Leuven (BE); Dries Braeken, Overpelt (BE); Liesbeth Micholt, Liedekerke (BE)

(73) Assignees: IMEC, Leuven (BE); Katholieke Universiteit Leuven, KU Leuven R&D, Leuven (BE)

( * ) Notice: Subject to any disclaimer, the term of this patent is extended or adjusted under 35 U.S.C. 154(b) by 0 days.

(21) Appl. No.: 13/519,894

(22) PCT Filed: Dec. 30, 2010

(86) PCT No.: PCT/EP2010/070947
§ 371 (c)(1),
(2), (4) Date: Sep. 19, 2012

(87) PCT Pub. No.: WO2011/080327
PCT Pub. Date: Jul. 7, 2011

(65) Prior Publication Data
US 2013/0045528 A1    Feb. 21, 2013

(30) Foreign Application Priority Data
Dec. 30, 2009  (EP) .................................... 09180939

(51) Int. Cl.
*C12M 1/42*     (2006.01)
*G01N 33/487*   (2006.01)

(52) U.S. Cl.
CPC ........ *G01N 33/48728* (2013.01); *C12M 35/02* (2013.01)

(58) Field of Classification Search
CPC .......................... G01N 33/48728; C12M 35/02
(Continued)

(56) References Cited

U.S. PATENT DOCUMENTS 8,452,369 B2 *   5/2013  Huys et al. .................. 600/372
2002/0110847 A1 *  8/2002  Baumann et al. ......... 435/287.1
(Continued)

FOREIGN PATENT DOCUMENTS

| EP | 1607743 A1 | 12/2005 |
| EP | 1967581 A1 | 9/2008 |

(Continued)

OTHER PUBLICATIONS

PCT International Search Report, PCT International Application No. PCT/EP2010/070947 dated Jul. 12, 2011.
(Continued)

*Primary Examiner* — William H Beisner
(74) *Attorney, Agent, or Firm* — McDonnell Boehnen Hulbert & Berghoff LLP

(57) ABSTRACT

The electronic device for sensing and/or actuating comprises a device surface to which an biological cell (40) is applied, further comprising a sensor and/or an actuator (25), and an access channel (20) with a channel port (21), said channel port being located in said surface. The access channel (20) is designed such that the biological cell (40) can enter the access channel (20) to thereby provide access to the sensor (25). Particularly the cell (40) forms a protruding portion (41) by entering the access channel (20), which portion is sensed. The access channel (20) may be provided with a specific sensor port at which the sensor (25) is present. The device may be used for sensing or actuating biological cells, such as neurons, for instance in electroporation treatments.

20 Claims, 5 Drawing Sheets

(58) Field of Classification Search
USPC .............................. 435/285.1, 285.2, 283.1
See application file for complete search history.

(56) References Cited

U.S. PATENT DOCUMENTS

2008/0097352 A1* 4/2008 Beck et al. ............... 604/272
2008/0319298 A1* 12/2008 Huys et al. ............... 600/377

FOREIGN PATENT DOCUMENTS

WO    WO95/33504    12/1995
WO    WO01/66065 A2    9/2001

OTHER PUBLICATIONS

Bergveld, Piet et al., "Extracellular Potential Recordings by Means of a Field Effect Transistor Without Gate Metal, Called OSFET", IEEE Transactions on Biomedical Engineering, vol. BME-23, No. 2, Mar. 1976, pp. 136-144.

Fromherz, Peter et al., "A Neuron-Silicon Junction: A Retzius Cell of the Leech on an Insulated-Gate Field Effect-Transistor", Sciences, New Series, vol. 252, No. 5010, May 31, 1991, pp. 1290-1293.

Fujimoto, Hiroyuki et al., "Electroporation Microarray for Parallel Transfer of Small Interfering RNA into Mammalian Cells", Anal. Bioanal. Chem., vol. 392, Oct. 24, 2008, pp. 1309-1316.

Han, Arum et al., "A Single Cell Multi-Analysis System for Electrophysiological Studies", Transducers '03, The 12th International Conference on Solid State Sensors, Actuators and Microsystems, Boston, Jun. 8-12, 2003, pp. 674-677.

Huys, Roeland et al., "Novel Concepts for Improved Communication Between Nerve Cells and Silicon Electronic Devices", Solid-State Electronics, vol. 52, No. 4, Apr. 2008, pp. 533-539.

Jaber, Fadi T. et al., "Action Potential Recording From Dielectrophoretically Positioned Neurons Inside Micro-Wells of a Planar Microelectrode Array", Journal of Neuroscience Methods, vol. 182, Jun. 11, 2009, pp. 225-235.

Kawano, Takeshi et al., "Neuron Size Si Probe Array Fabricated on Integrated Circuits for Multichannel Electrode", Transducers '03, The 12th International Conference on Solid State Sensors, Actuators and Microsystems, Boston, Jun. 8-12, 2003, pp. 1679-1682.

Kawano, Takeshi et al., "Three-Dimensional Multichannel Si Microprobe Electrode Array Chip for Analysis of the Nervous System", Electron Devices Meeting, IEDM Technical Digest, IEEE International, Dec. 13-15, 2004, pp. 1013-1016.

McAllister, Devin V. et al., "Microfabricated Microneedles for Gene and Drug Delivery", Annu. Rev. Biomed. Eng., vol. 2, Aug. 2000, pp. 289-313.

Cohen, Ariel et al., "Depletion Type Floating Gate p-Channel MOS Transistor for Recording Action Potentials Generated by Cultured Neurons", Biosensors and Bioelectroincs, vol. 19, Jan. 14, 2004, pp. 1703-1709.

Braeken, Dries et al., "Local Electrical Stimulation of Single Adherent Cells Using Three-Dimensional Electrode Arrays With Small Interelectrode Distances", 31st Annual International Conference of the IEEE EMBS, Minneapolis, Minnesota, USA, Sep. 2-6, 2009, pp. 2756-2759.

\* cited by examiner

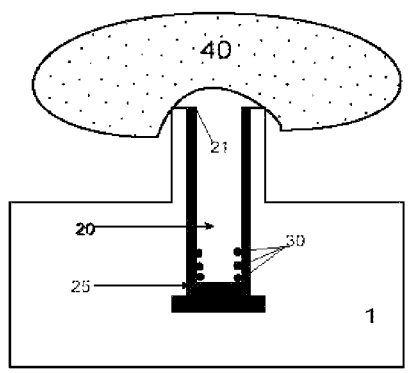
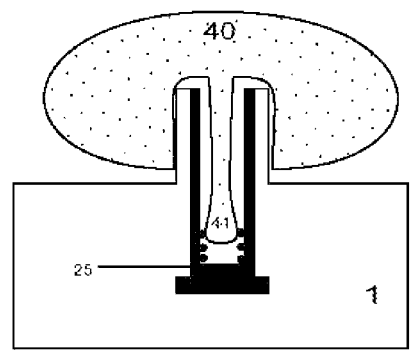
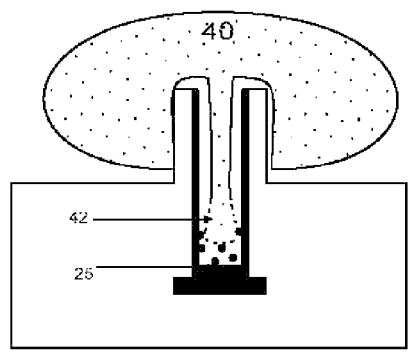
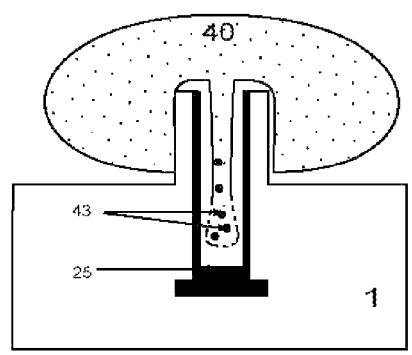
Fig. 5A-D
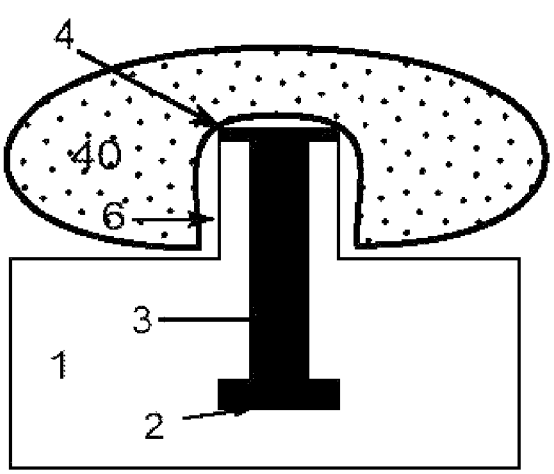
Fig. 9 prior art

MICRONEEDLE

CROSS-REFERENCE TO RELATED APPLICATIONS

The present application is a U.S. national stage application of International Application Serial No. PCT/EP2010/070947 filed Dec. 30, 2010, which claims priority to European Patent Application No. 09180939.2 filed Dec. 30, 2009, the contents of which are hereby incorporated by reference.

FIELD OF THE INVENTION

The invention relates to an electronic device for sensing and/or actuating, comprising a device surface to which a biological cell can be applied and means for sensing and/or actuating said biological cell.

The disclosure further relates to the use of such an electronic device.

BACKGROUND OF THE INVENTION

Sensors comprising micro-electrode arrays are used for measuring electrical activity in small networks of biological cells, such as neurons. Theses sensors are often relatively big and only small matrices or arrays of micro-electrodes can be made. Current state-of-the-art micro-electrode arrays (MEAs) may contain a maximum of 64 electrodes with a minimal spacing of 100 μm between neighbouring electrodes. The electrodes are often made of flat TiN pads with a diameter of maximum 10 μm. For some applications, smaller spacings, e.g. <10 μm, and a larger number of electrodes, e.g. >60000, may be required.

On-chip single cell recording of electrical activity using field-effect transistors has been demonstrated for large neurons or tissue slices (see P. Bergveld et al, IEEE Transactions on Biomedical Engineering, 1976. P. Fromherz et al., Science, May 1991, A. Cohen et al, Biosensors and Electronics, January 2004). In the case of mammalian neurons, e.g. hippocampal neurons, the cells are much smaller, which leads to a less efficient electrical coupling onto the chip surface and make a reliable electrical contact between the cell membrane and the recording device.

Hoogerwerf et al. have disclosed an array of microneedles for sensing of neurons. The array of microneedles or probes is assembled to a silicon platform with a construction in which the microneedles run through holes in the platform and then are connected using a certain flange. Electrical connection is made with bumps, e.g. eutectic metal bumps or plated contacts on a plated gold beam. The beams are coupled to interconnects extending on the substrate flange and from there extend on the microneedles. Such needles are particularly suitable for probing a cell. The overall array with microneedles bears a large similarity to probe cards with a plurality of probes used for testing integrated circuits. The conductive probes of such an array make contact with selective test pads on the integrated circuits and provide series of suitably digital signals to the integrated circuit for testing proper operation. However, when applying such array of probes to a biological cell, an adequate measuring of cell properties turns out difficult. The cell membrane does not have a solid and fixed plate of test pads. Therefore, an adequate stimulation by electric pulses and subsequent measuring is not achievable.

Fujimoto et al. disclose "Electroporation microarray for parallel transfer of small interfering RNA into mammalian cells" in Analytical and Bioanalytical Chemistry, Springer, Heidelberg, Del., Vol. 392, no. 7-8, 12-2008, pages 1309-1316. The document recites transfer of chemical substances into living cells, specifically transfer of siRNA into mammalian cells by an electroporation microarray.

Braeken et al. disclose "Local electrical stimulation of single adherent cells using three-dimensional electrode arrays with small interelectrode distances" in Engineering in Medicine and Biology Society 2009, Annual Int. Conf. IEEE, IEEE, Piscataway, N.J., USA, Vol. 1, 3 Sep. 2009, pages 2756-2759. The document recites cell electroporation by applying voltage pulses by a microneedle being smaller than the cell.

Han et al. disclose "A single cell multi-analysis system for electrophysiological studies" in Transducers '03, $12^{th}$ Int. Conf. Solid State sensors, actuators and Microsystems, 2003, IEEE, Piscataway, N.J., USA, Vol. 1, 9 Jun. 2003, pages 674-677. The document recites a micro analysis system for multi purpose electrophysiological studies of single cells. It recites an electrode at a sidewall for coupling between a cell and an electrode.

Huys et al. disclose "Novel concepts for improved communication between nerve cells and silicon electronic devices" in Solid State Electronics, Elsevier Science Publishers, Barking, GB, Vol. 52, no. 4, 3 Dec. 2007, pages 533-539. The document recites a high density matrix of sensors and actuators on a CMOS chip. The document recites that electrical coupling can be improved by increasing the contact area between cell and electrode.

Jaber et al. disclose "Action potential recording from dielectrophoretically positioned neurons inside micro-wells of a planar microelectrode array" in J. Neuroscience Methods, Elsevier Science Publishers, Amsterdam, NL, Vol. 182, no. 2, 15 Sep. 2009, pages 225-235. The document recites 4×4 planar microelectrode arrays for studying and organising in vitro neural networks at a cellular level. The document recites growth of a biological cell into a channel, and sensing and actuating a portion of the cell.

EP-A 1967581 discloses CMOS compatible microneedles. A diagrammatical cross-sectional drawing hereof is shown in FIG. 9. The microneedles 6 are present on a substrate 1. The compatibility with CMOS is enabled, in one embodiment, with a manufacturing process as typically in use for the manufacture of interconnect structures of integrated circuits. While Hoogerwerf et al provide contacts on the outside of the microneedle, EP1967581 defines conductors 3 and/or microfluidic channels inside the microneedle 6. Thereto a dielectric matrix with a conductor 3 on top of an interconnect 2 is defined. Subsequently, the dielectric matrix is patterned so as to define the microneedles 6 with an insulating shaft around the conductor.

The use of such CMOS compatible technology for manufacturing results therein that a top surface of the microneedle may be planar. This is particularly the case at a stage during processing of the microneedles, before the partial removal of the dielectric matrix around the microneedles. As a result, a sensor or actuator device 4 may be defined on top of the microneedle 6. The interconnects 3 and/or microfluidic channels then run towards the sensor or actuator device 4 on top of the microneedle 6. On application of a biological cell 40, engulfment of the microneedle 6 has been found. This engulfment is beneficial as it leads to reduction of the amplitude of a stimulation current for the actuation of the biological cell.

However, it turns out that the area of the sensor or actuator device on top of the microneedle is limited. Increase of the area by increasing the diameter of the microneedle turns out limited, as the engulfment of the microneedle 6 by the biological cell 40 may be lost, which is undesired.

SUMMARY OF THE INVENTION

It an object of the invention to provide an alternative electronic device for sensing and/or actuating, comprising a device surface to which a biological cell is applied and means for sensing and/or actuating said biological cell.

An advantage of such an electronic device is that it allows improved sensing and/or actuation of a biological cell. It is a further object to use such a device for sensing purposes.

According to a first aspect, an electronic device for sensing and/or actuating is provided, comprising:
- a substrate with a device surface to which a biological cell can be applied, and
- an access channel with a channel port, said channel port being located in said device surface, which access channel has a longitudinal axis extending in a direction substantially perpendicular to a plane through said substrate, which access channel has a restricted volume and an internal surface that is substantially closed except for the channel port, and which access channel further comprises means for sensing and/or actuating the biological cell, such that a protruding portion of the biological cell can enter the access channel to thereby provide access to the means for sensing and/or actuating.

The device comprises a device surface to which a biological cell is to be applied. The device further comprises an access channel with a channel port, said channel port being located in said surface. The access channel has, in one embodiment, a longitudinal axis extending in a direction substantially perpendicular to a plane through said channel port. The access channel further has, in one embodiment, a restricted volume and an internal surface that is substantially closed except for the channel port. Herein the access channel comprises a sensor and/or actuator for sensing or actuating the biological cell, such that the biological cell is provided access to the sensor and/or actuator, e.g. by entering the access channel.

It has been found by the inventors of the present invention, that a biological cell, once adhered to a surface with its cell membrane may begin to grow and thus form protruding portions within shapes suitable for such protruding portions.

This finding has been exploited in the present invention in that the said shape is used as an access channel to the sensor or actuator. In other words, the sensor or actuator is now not located at a top surface of a microneedle, but within an access channel with an internal surface that is closed except for the channel port. Access to the sensor is obtained only after that the biological cell has sufficiently adhered to the device surface so as to begin to form a protruding portion within the access channel. It is also the protruding portion upon which the sensing is carried out. Since the protruding portion is however in direct contact with the rest of the biological cell without any intermediate interruption, such measurements are deemed representative of the complete cell and/or can be transformed into results representative for the complete cell on the basis of some calibration results.

In one important embodiment, the device surface has a non-planar shape with an extended surface area. More advantageously, the device surface comprises a portion extending from a substrate, said extended surface area being at least twice of a reference surface area defined by perpendicular projection on the substrate. It has been found in experiments leading to the invention that a proper adhesion is improved by extending the surface area into a non-planar shape. One suitable non-planar shape is for instance the provision of a cavity surrounded by one or more wall shaped portions extending from a substrate, within which cavity the channel port of the access channel is defined. The term 'device surface' as used herein specifically refers to the surface within an area in which adhesion or more particularly engulfment occurs.

Particularly good results have been obtained with microneedles. It has been observed, that biological cells will engulf the microneedles of EP-A 1967581. Such engulfing gives rise to a particularly tight coupling between the cell membrane and the surface of the microneedle. The engulfing further improves the electrical coupling between the sensor or actuator and the cell membrane.

In addition to or instead of increasing surface area of the device surface, attraction between the surface and the biological cell may be improved by functionalizing the device surface or portions thereof. Specific functionalizations may be of chemical and/or of electrical nature. An example of a functionalization of a chemical nature is the application of one or more self-assembled monolayers comprising dedicated functional groups. Typical monolayers use thiol as linking groups to a Au surface. Good results may further be obtained with siloxyl-linking groups. Advantageous forms of such monolayer compounds may include protein-resistant chains such as oligoalkylene glycol groups and recognizing or pre-activated groups for binding to the cell membrane. Typically, such pre-activated group is a polar group. Suitable silane compounds and their synthesis are for instance known from EP1607743 A1.

In one embodiment, the access channel is further provided with a sensor port, at which a sensor is present. Preferably, this sensor port is located at a bottom of the access channel. However, alternatively, the access channel may give access to a cavity, at a surface of which the sensor is present. The advantage of such cavity is that a sensor with a larger surface area may be provided. The sensor is for instance a chemical sensor, such as a pH-sensor. Though experiments typically use isotonic fluids, a chemical reaction may occur at a cell membrane giving rise to deviations of the pH, for instance.

The access channel comprises an electrode at a sidewall of the access channel so as to sense and/or actuate the protruding cell portion, for instance by capacitive coupling. The operation of the electrode by means of capacitive coupling could be understood in analogy to the operation of the gate electrode of a field effect transistor: application of a voltage on the electrode will influence a charge distribution within the protruding portion of the biological cell. Variation of the applied voltage may stimulate the protruding portion of the cell to certain behaviour. Such behaviour could turn out to mimic behaviour in cells known to occur, but currently not understood. An example hereof is failures in signal transmission between cells and/or pain observations by patients as a result thereof. Such behaviour could also be stimulated so as to carry out a treatment on a patient. The operation of the electrode is enhanced by enlarging its surface area. It is therefore advantageous that the electrode substantially covers a complete inner surface of the access channel.

In a particular implementation hereof, the access channel with the electrode on its surface is used as an actuator, for stimulating the cell. A sensor is provided at a location distinct from the access channel. The sensor is used to sense changes occurring as a result of the actuation within the access channel. The location distinct from the access channel may be within another access channel, for instance at a channel port thereof. However, alternative locations are not excluded. One example is a sensor being present in or on a sensing microneedle, that is also engulfed by the cell. Suitably, the sensor is present at a sensor port of an access channel within the sensing microneedle.

In another embodiment of the invention, a sensor device is provided. The sensor device comprises at least one microneedle on a substrate, which microneedle comprises an access channel with a channel port and a sensor port, which access channel is designed for providing access to a protruding portion of a biological cell to be applied on and/or around the microneedle, which channel port being located at a tip of the microneedle, which access channel is suitably surrounded by a shaft of insulating material. The sensor device further comprises a sensor located at the sensor port.

In another embodiment of the invention, an electronic device for sensing and/or actuating is provided. The electronic device comprises at least one microneedle on a substrate provided with an access channel with a channel port located at a tip of the microneedle. The access channel is designed for providing access to a protruding portion of a biological cell to be applied on a device surface, e.g. in a cell adhesion area, on and/or around the microneedle. The access channel has a longitudinal axis extending in a direction substantially perpendicular to a plane through said substrate. The access channel has a restricted volume and an internal surface that is substantially closed except for the channel port, and it comprises an electrode at a sidewall for actuating the protruding cell portion.

According to again another aspect of the invention, a method of sensing and/or actuating a biological cell is provided. The method comprises the steps of:
  providing an electronic device according to the invention,
  providing a biological cell to the device surface, preferably such that the cell adheres to a cell adhesion area;
  allowing growth of a protruding portion of the cell into the access channel, and
  sensing and/or actuating of the protruding portion of the cell in the access channel.

BRIEF DESCRIPTION OF THE FIGURES

FIG. 5*a-d* shows in diagrammatical, cross-sectional views a series of steps of the use of the device of the invention for electroporation of a biological cell;

FIG. 9 shows a diagrammatical, cross-sectional view of a prior art device.

DETAILED DESCRIPTION OF THE FIGURES

Figure 1:
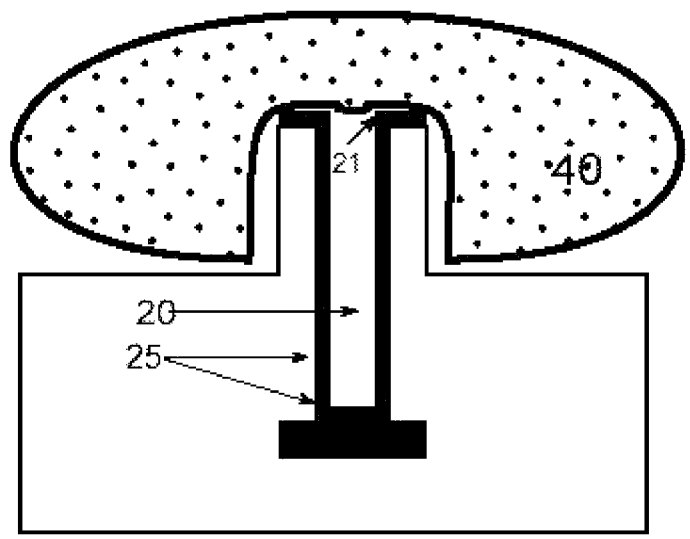
FIG. 1 shows a diagrammatical, cross-sectional view of the device of the invention in a first embodiment.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention. Same reference numerals in different figures refer to equal or like elements.

Figure 2:
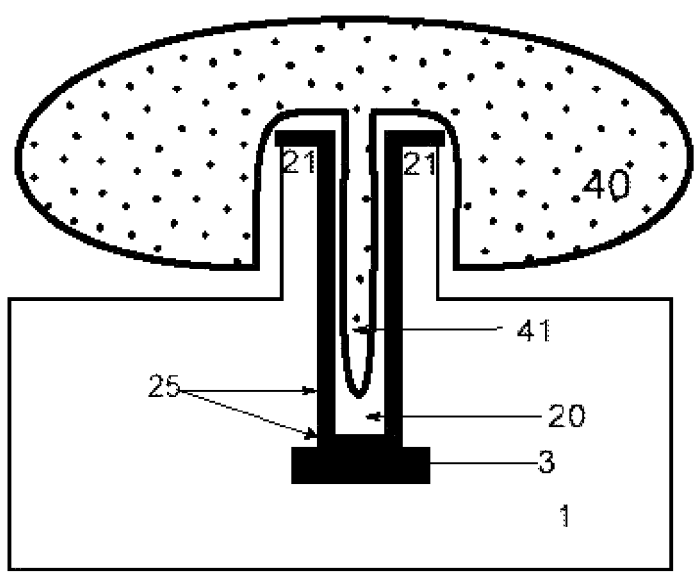
FIG. 2 shows a diagrammatical, cross-sectional view of the first embodiment after that a biological cell has formed a protruding portion into the access channel.

FIG. 1 shows a diagrammatical, cross-sectional view of the device according to the invention in a first embodiment just after application of a biological cell to the device. FIG. 2 shows the device of the first embodiment in a second state, after which a cell has entered the access channel 20. The device comprises a device surface. The device further comprises an access channel 20 with a channel port 21. The channel port 21 is located within the surface. The access channel 20 has a longitudinal axis A, which in this example, extends substantially perpendicular to a plane through the channel port 21, or alternatively, a plane through a substrate. The access channel 20 has a restricted volume and an internal surface that is substantially closed except for the channel port 21. The term 'substantially closed' is understood to mean within the context of the present application, that a further port, such as a chemical port discussed later on, is present within the access channel 20. Such further port is however an option. The access channel may thus further be closed except for the channel port.

The access channel 20 further comprises means 24,25 for sensing and/or actuating. This is done so that by entering the access channel 20, the biological cell 40 is provided access to those means 24,25 for sensing and/or actuating. The means for sensing and/or actuating may refer to an electrode, such as a conductive layer, a sensor, an actuator, or a combination thereof. This location for the means 24,25 for sensing and/or actuating implies that said sensing and/or actuating is applied to that portion 41 of the cell 40 that has entered the access channel 20. This portion is herein also referred to as a protruding portion 41 of the cell. It is understood that this protruding portion 41 is not present when the biological cell 40 is applied. It is formed by virtue of the template shape offered by the access channel 20.

Thus, one may distinguish different phases in the method of the invention. First, a biological cell 40 is applied. While this application process could be a specific application of individual cells to the device surface, it is suitably a process in which a fluid, e.g. a free culture medium, with a plurality of biological cells is applied. Individual cells thereafter move to the surface. This movement may be caused by diffusion, convection, electromagnetic attraction, for instance by application of a voltage difference, or a combination of such effects.

Suitably, the device surface is designed or treated such that the cell wets the surface. Surface wetting of surfaces is governed by surface tension between the surface material and the liquid present on the surface, and typically expressed by means of the contact angle. The degree of wetting is determined by a force balance between adhesive forces, e.g. attracting liquid molecules to the surface, and cohesive forces, e.g. attracting liquid molecules to each other. Preferably, the surface is hydrophilic. Most suitably, the surface area is increased in that the surface has a non-planar shape, such as a surface of a microneedle or a cavity surface. This will further shift the force balance towards adhesion. This process may be enhanced by geometrical factors. Most suitably such factors enable that an outside, non-adhered portion of the biological cell has an optimized, ideally minimum, surface area. This is for instance achieved by engulfment of a microneedle through the cell 40.

It is observed that said adhesion process wherein surface wetting occurs may be further improved by application of a suitable surface treatment. One of such surface treatments is the functionalization of the device surface. As a consequence hereof, the mere adhesion may be strengthened by bonding to the surface. This bonding could be a molecular bond, but alternatively hydrogen bonding, as well as Van der Waals bonding reflecting dipole/dipole and/or dipole/induced dipole interactions.

Subsequently, the cell 40 as present on, i.e. adhered to, the device surface, may enter the access channel 20. This entering turns out not comparable to the process in the previous steps resulting in engulfment. In fact, the inventors believe without desiring to be bound by following hypothesis, that growth occurs such that the protruding portion 41 of the cell 40 begins to be formed in the access channel 20. Such protruding portion 41 may be formed with all types of different cells 20. In one scientifically and medically interesting application, the cell 40 is a neuron. The protruding cell portion 41 may be, in that example, a synapse.

Factors that may contribute to growth of the protruding portion 41 are for instance an effective diameter of the access channel 20, as measured at the channel port; the inside surface of the access channel 20 being wettable by the cell membrane 40; a surface that is sufficiently smooth, such that growth or movement of the cell membrane is not hampered by any restrictions; a circular or oval shape as seen in cross-sectional view in a plane substantially parallel to the channel port is preferred. Hence, the access channel is free of corners into which the protruding portion of the cell does not fit. Another contributing measure is the provision of the access channel at the channel port with an increasing diameter. The intention of the latter measure is to prevent a sharp edge between the inner surface of the access channel and the device surface.

One advantage of the provision of the means for sensing and/or actuating inside the access channel is that sensing and/or actuating is (only) applied to that portion 41 of the cell 40 that has entered the access channel 20. This protruding portion is a portion with a limited volume that is nevertheless an integral part of the biological cell 40. It is moreover such that such protruding portion of the cell 40 has less space or opportunity of diffusion that any portion on a flat surface. This makes that sensing and/or actuating of the cell 40 may be carried out in a more controlled manner and hence is better repeatable.

A further advantage of the provision of the means for sensing and/or actuating inside the access channel is that specific reactions may be carried out and/or may be stimulated to occur which are less feasible—if at all—on a substantially planar surface. One such reaction is electroporation of the cell membrane, another such reaction is synaptogenesis.

In the embodiment of FIG. 1, an electrode 25 extending along the internal surface of the access channel 20 constitutes said means for sensing and/or actuating. Though preferable, it is not necessary that the electrode 25 covers the complete internal surface of the access channel. The electrode 25 may be covered with a dielectric layer, such as an oxide or a nitride. An interconnect 3 is present for applying voltages to the electrode 25. Suitably a diffusion barrier—not shown—is present, for instance of SiC, so as to isolate an underlying substrate 1 from the access channel 20. This diffusion barrier is found to reduce cytotoxicity. In this embodiment, but this is not essential, the device surface has a non-planar shape with an extended surface area. Particularly, as shown in FIGS. 1 and 2, the non-planar shape is designed so as to enable that the biological cell 40 engulfs the device surface. In this example, the device surface has a portion extending substantially in parallel to the longitudinal axis A of the access channel 20, i.e. at the outside of a block-shaped, a cylinder-shaped or a pillar-shaped body. This body is in a most advantageous embodiment a microneedle, i.e. a structure oriented substantially perpendicular to the plane of the substrate and having a width between 50 nm and 10 µm, for example between 100 nm and 6 µm and a height of between 150 nm and 50 µm. The microneedle may be a shaft of insulating material. Most suitably, the access channel 20 is trench shaped, with a oval or circular cross-section parallel to the plane of the channel port. However, it is not excluded that the access channel is is provided with an chemical port. Reagents may be present at the chemical port or be transported to said chemical port, for instance by means of a microfluidic channel. It is moreover not excluded that the trench-shaped channel may be provided with a widened portion at its bottom.

The access channel has an aspect ratio of depth over diameter of more than 1. Preferably, said aspect ratio is 5 or higher, more preferably said aspect ratio is 10 or higher. The access channel suitably has a diameter in the range of 0.1 to 8 µm, preferably 1 to 7.5 µm, more preferably 3 to 7 µm. The access channel suitably has a depth in the range of 0.3 to 15 µm, preferably 1 to 8 µm. In case that the access channel 20 is present within a microneedle or another body extending from a substrate, the access channel may have a height larger, equal or smaller than said microneedle. Its height may thus be tuned to a specific cell type. In case that the height of the access channel is larger than that of the microneedle, this may be achieved by continued etching into an underlying substrate. Alternatively, it may be achieved by covering the substrate outside the microneedle with one or more layers. This effectively reduces the height of the microneedle. Such covering may be achieved by deposition or growth of certain materials, but alternatively by merely partial removal of a template layer while forming the microneedle.

In a further embodiment, functionalization of the access port and/or inner surface—also referred to as sidewall—of the access channel 20 with proteins or peptides is provided. The said functionalisation attracts the biological cell 40 or the protruding portion 41 of the biological cell 40. Suitable examples of molecules providing functionalization include poly-L-Lysine, laminine, peptides such as RGD and PA22-2. The functionalization may be applied, for instance, with chemisorption and through self-assembled monolayers.

In an even further developed version hereof, the functionalization triggers a specific reaction in the cell. Examples of suitable molecules for this purpose include glutamate receptors, glutamate antibodies, integrines. Examples of reactions that may be triggered include the promotion of focal adhesion as well as certain reception expressions on or in a membrane of the cell.

Figure 3:
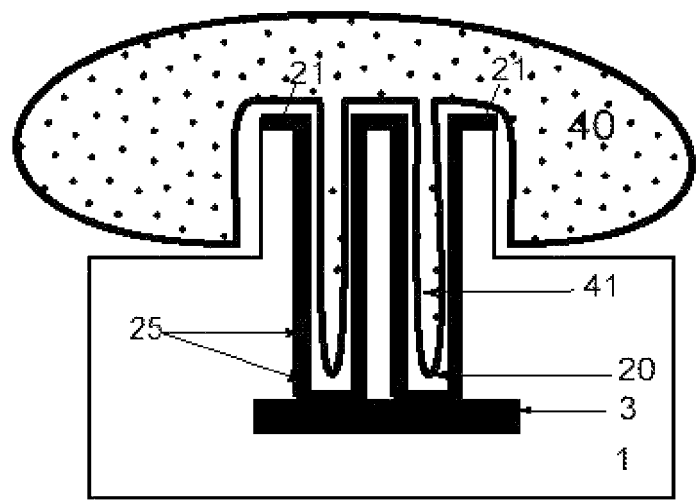
FIG. 3 shows a diagrammatical, cross-sectional view of the device of the invention in a second embodiment.
Figure 4:
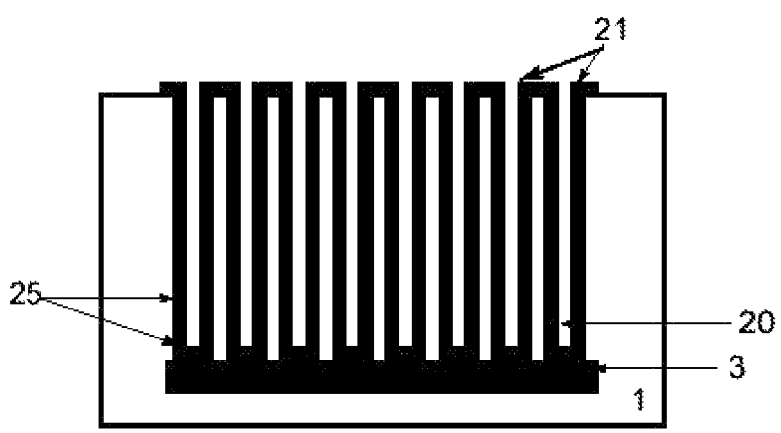
FIG. 4 shows a diagrammatical, cross-sectional view of the device of the invention in a third embodiment.

FIG. 3 shows a diagrammatical, cross-sectional view of a further embodiment according to the invention, in which a first and a second microneedle, each with an access channel 20 are provided. The electrode 25 extends on the inner surfaces of both microneedles. Herewith the effective surface area for stimulating protruding portions of the biological cell 40 is substantially increased. In this non-limiting embodiment, the electrode is continuous along the tip of the microneedles and the inner surfaces of both microneedles. FIG. 4 shows a diagrammatical, cross-sectional view of another embodiment according to the invention. This embodiment is most suitably manufactured in accordance with the third method as specified above. It comprises a plurality of access channels 20 parallel to each other and defined within the substrate 1. The plurality of access channels 20 comprises preferably more than 5 access channels, more preferably at least 10 access channels and even more preferably an array of at least 20 access channels. The advantage of this embodiment is a substantial increase in surface area of the electrode 25. Stronger stimulation of the cell may thus be provided. Furthermore, sections of the array of access channels may be isolated to study local differences in behaviour of the cells.

Figure 6:
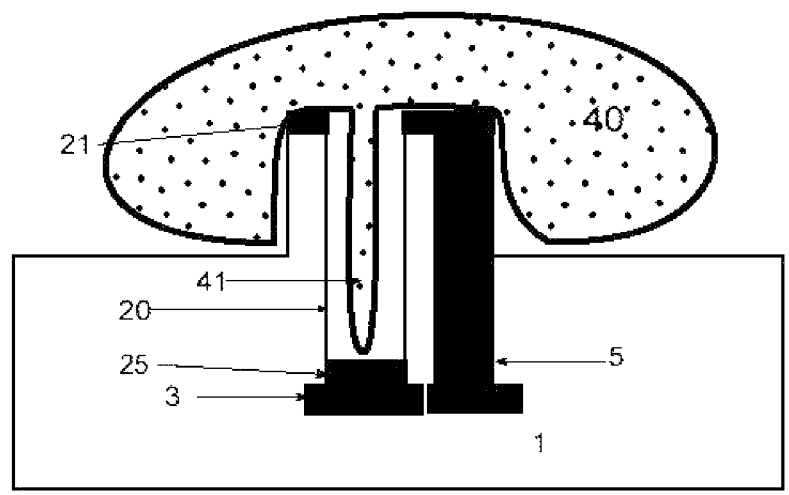
FIG. 6 shows a diagrammatical, cross-sectional view of the device of the invention in a fourth embodiment.

FIG. 6 shows a diagrammatical, cross-sectional view of a further embodiment according to the invention. Herein, the microneedle comprises a vertical conductor 5 in addition to the access channel 20. The advantage hereof is that a separate sensor and/or actuator may be present on the tip of the microneedle. Particularly, the provision of a sensor is deemed beneficial. It is therewith possible to detect changes in the cell outside the protruding portion 41. When in use as an actuator, it may be beneficial for stimulating the cell to grow into the access channel 20.

Figure 7:
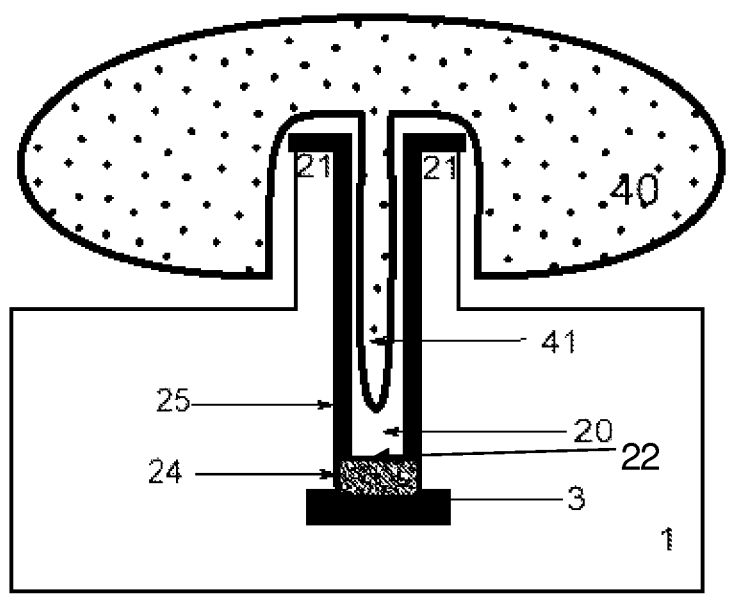
FIG. 7 shows a diagrammatical, cross-sectional view of the device of the invention in a fifth embodiment.

FIG. 7 shows a diagrammatical, cross-sectional view of again another embodiment according to the invention. Herein a sensor 24 constitutes a means for sensing and/or actuating. The sensor 24 is provided at a sensor port 22, preferably at a bottom of the access channel 20. Suitably, the sensor 24 is manufactured in or directed on top of the semiconductor substrate 1. The sensor may be a capacitive sensor, a transistor type sensor, for instance of the type known as a chemFET, a chemical sensor, for instance a pH-sensor. Particularly the sensor may be tuned for sensing one or more properties occurring during electroporation of the biological cell.

Figure 8:
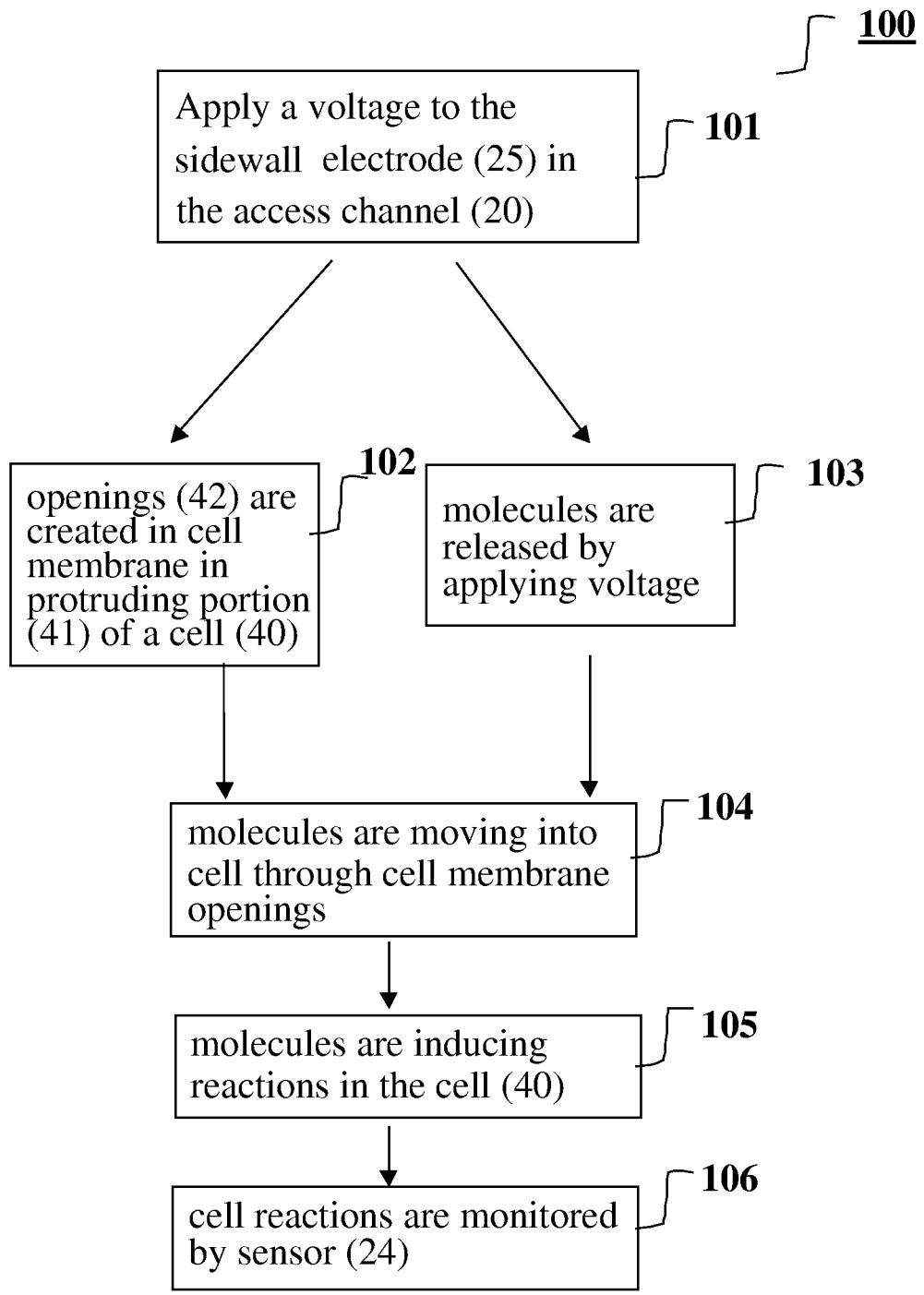
FIG. 8 shows a flow diagram of the use of the device of the invention for electroporation of a biological cell.

FIG. 8 shows a sequence 100 of steps occurring in electroporation. In a first step 101, voltage pulses are applied. The voltage of the pulses is preferably in the range of 200 mV-10V. The pulses are preferably applied with a duration of nanoseconds, and with a frequency suitably in the range of 1 MHz to approximately 1 GHz.

The result of the application of voltage pulses is shown as step 102: openings are created in the cell membrane of the cell. The threshold voltage for formation of such openings depends on the effectiveness of the coupling between the electrode and the cell membrane. The coupling is moreover enhanced by increasing surface area.

Step 103 occurs preferably simultaneously with the generation of said openings in the cell membrane. Herein, a reagent is released into the access channel 20 for interaction with the cell. The reagent may be released as molecules or ions. The reagent may be present, prior to release, at a chemical port in the access channel. It may be provided there during or after manufacture of the device. It may be there in solid form or in a fluid form, e.g. as a solution, suspension, dispersion or (viscous) liquid. When in fluid form, the reagent is suitably transported to the chemical port by means of a microfluidic channel. Alternatively, the reagent may be present in functionalized form on the inner surface of the access channel. Self-assembled monolayers may be used for such functionalization. The simultaneous occurrence of the release of the reagent (step 103) and the formation of openings (102) may be achieved by choosing a functionalisation that starts release upon application of voltage pulses. However, the release of the reagent may further be initiated differently. For instance, it could be initiated through the provision of culture medium into the access channel. In one specific implementation, the reagent is present in a bottom part of the access channel. When the cell subsequently enters the access channel, the reagent is present.

Steps 104 and 105 show subsequent steps, in which the reagent first diffuses into the cell through the formed openings in the cell membrane, and thereafter induces a reaction or a physical change in the cell. Again, this is effectively a subsequent phase of the method and the result of the previous step. One suitable reagent is for instance a metal ion, such as an alkali metal ion or an earth alkali metal ion, for instance $Ca^{2+}$. The amount of metal ion diffused into the cell can subsequently be measured electrically. Molecules suitable for functionalization are for instance glutamate enzymes, acetylcholine-enzymes.

Step 106 shows the sensing of changes resulting induced reaction or induced physical change. The sensing is preferably carried out with the sensor within the access channel. However, this is not essential and a sensor at a location differently could be used alternatively.

FIG. 5A-D show in a series of cross-sectional views the use of the device for electroporation for further explanation. This use is particularly carried out with a device as shown in FIG. 7.

FIG. 5A shows the presence of the cell 40 prior to the formation of the protruding portions 41. The access channel 20 comprises in this embodiment a sensor 25 at a sensor port and a reagent 30. The reagent 30 is in this embodiment present in functionalized and adhered form at an inner surface of the access channel 20.

FIG. 5B shows the situation after formation of the protruding portion 41 in the access channel 20. This view corresponds to the starting situation of the flow diagram of FIG. 8. Though the figure shows a sharp angle between the cell and the protruding portion, this is not understood to represent reality appropriately. Additionally, it is believed that the insertion of the cell into the access channel 20 occurs along the inner surface thereof.

FIG. 5C shows the situation after release of the reagent 30 into the access channel (step 103), caused by the application of an adequate voltage (step 101). Electroporation (step 102) is also indicated in this Figure. The reagent 30 is herein shown as droplets within the access channel 20. This may occur with certain reagents having a hydrophilic head and a hydrophobic tail. Such reagents may form small vesicles with the heads at the outside and the tails at the inside. However, it is not deemed necessary that the reagent flows from the inner surface to the protruding portion 41 of the cell in droplet-like structures. The reagent 30 may alternatively dissolve in a culture medium within the access channel 20.

FIG. 5D shows the subsequent situation, after the diffusion of the reagent 30 into the cell 40 (step 104). A reaction may now be induced and resulting changes may be measured, for instance with the sensor 25.

Synaptogenesis is the formation of distinct synaptic specialisations. It involves a complex series of events, spanning neuronal differentiation and localized induction of presynaptic and postsynaptic differentiation.

Manufacture of the Device

The device as shown in FIG. 7 may be obtained through various manufacturing methods. According to a first method, a standard CMOS-metallisation/back-end process is used to fabricate said microneedles. This back-end process is carried out on top of a substrate, for example a silicon wafer or a silicon-on-insulator wafer. Devices are suitably defined in the substrate according to known methods, including in one embodiment (as shown in FIG. 7) a sensor 24. Metal interconnects as far as needed were embedded in silicon oxide and fabricated using a Cu damascene process. An etch stop layer made of for instance SiC, TiN, $Si_3N_4$ was deposited on the metal.

Subsequently, a relatively thick layer of dielectric material is deposited. Preferably, the dielectric layer is non-porous. The dielectric material is for instance an organic dielectric or an oxide, such as silicon oxide. A suitable deposition technique is PECVD, but alternatives such as a spin-on oxide are not excluded. The dielectric layer was patterned to define the access channel 20 aligned with the sensor underneath, particularly using deep-reactive ion etching. In order to expose the sensor at the sensor port, the etch stop layer is locally removed in the access channel. The diameter of the hole ranged in one experiment from 250 nm to 1 µm, but other diameters could be chosen as well.

An electrically conductive layer 25 was thereafter deposited in the access channel 20. An adhesion layer may be deposited prior to the conductive layer 25. The conductive layer may again by covered by a thin dielectric layer, such as an oxide or a nitride. Aluminum (Al) and Tungsten (W) are suitable materials for the electrically conductive layer 25, particularly when not covered by an additional dielectric layer. It has a low toxicity. In one embodiment, a plurality of layers jointly constituting a sensor or an actuator are deposited as conformal coatings in the access channel 20. Materials such as iridium oxide and titanium nitride are suitable for inclusion in a stack operating as a sensor or an actuator. The access channel 20 may thereafter filled with a sacrificial layer, which may be a resist also used for patterning in a subsequent step.

Subsequently, dots of resist are formed on the top of the dielectric layer at locations which are not to be removed. The dots covering said locations are slightly larger than the diameter of the access channel 20. The extra area of the dots, i.e. the area larger than the diameter of the access channel 20, defines the width of the body surrounding the access channel 20. The dots may have a diameter of between 100 nm and 6 µm or between 600 nm and 1200 nm. Thereafter, the insulating layer may be etched, for instance by deep reactive ion-etching, leaving a shaft of insulating material of between 50 nm and 1 µm, for example between 100 and 200 nm surrounding the access channel 20. The total width or diameter of the body, e.g. the microneedles may be between 100 nm and 6 µm, for example between 600 and 1200 nm. Finally, both the dots of resist and the sacrificial layer are removed.

If desired, a via may be provided in the dielectric layer prior to definition of the access channel. This via defines an electrical connection to the tip of the microneedle allowing the provision of an additional sensor and/or actuator thereon. The additional sensor or actuator is for instance an electrode. Instead of being present within the same microneedle, such via could be present in an adjacent microneedle.

According to a second implementation of manufacturing the devices according to the invention, the electrodes are defined in platinum (Pt). The manufacture started again with the definition of interconnects, for instance of Cu, as deposited on an insulating layer on a silicon wafer. A suitable pattern comprises for instance interconnects with a thickness of 200-500 nm embedded in a dielectric layer, for instance silicon oxide. A subsequent dielectric layer, for instance with a thickness in the range of 500 nm to 3 µm is provided thereon. Access channels 20 were plasma etched into the dielectric layer. Thereafter, a seed layer, for instance a Au seed layer was deposited, for instance by sputtering on the dielectric layer and in the access channels, after a cleaning step. Unwanted portion of the seed layer, i.e. on the top surface were removed, for instance by mechanical polishing. Thereafter, the semi-manufactured device, preferably a set of semi-manufactured devices present on one substrate such as a wafer, were immersed into a solution for a galvanic replacement reaction. In one example, the solution contained a hexachloroplatinic acid hydrate ($H_2PtCl_6$)-solution with a concentration of 40 mM. The reaction time was, in one example, varied between 30 and 180 seconds. Strong magnetic stirring was applied. The prepared wafers were rinsed by DI-water and then dried with a nitrogen gun. Subsequently, the dielectric layer, in one example silicon oxide, was etched in a buffered HF solution (BHF, 7:1) for 4-5 minutes to expose the Pt nanoshell tubes, and thereafter rinsed with DI-water.

According to a third implementation of the method, the starting template was a semiconductor substrate, for instance of silicon. A mask, for instance of silicon oxide, was provided on the silicon wafer according to a desired pattern. Access channels (i.e. trenches) were etched into the silicon using deep reactive ion etching. Subsequently, surfaces of the access channels were made highly conductive by implantation of dopants. Thereafter, one or more dielectric layers, were deposited. A contact was established adjacent to the trench within the area in which dopants were implanted. Suitably, the access channels were covered with a sacrificial layer. Further layers, such as interconnects and suitably a protrusion around the access channel, were provided so as to optimize the device layout. Finally, the sacrificial layer was again removed.

Example

A body in the form of a microneedle is provided. The body comprises an oxide with a height of 6 µm. Its diameter is in the range of 2.5 µm to 1.8 µm. An access channel 20 is present inside the microneedle body 15, so that the oxide forms a shaft around the access channel 20. The access channel 20 is defined with a diameter from 0.5 to 1.5 µm. Spacing between individual microneedles ranges from 3 µm to 1 µm. The body with the access channel was manufactured in accordance with the first embodiment of the manufacturing process as outlined above. A layer of TiN is present on top of the microneedle.

Mouse hippocampal neurons are isolated from embryonic day 17 (E17) mice embryos. Before seeding, the surface is coated with poly-L-lysine to improve to adhesion of the cells. The neurons are then seeded on the microneedles.

After 1 to 3 days in vitro (DIV), cells are fixed with formaldehyde. Before confocal microscopy imaging can be done, cells must permeabilized with 0.5% Triton X100 and stained for with Phalloidin 488 to visualize the actin filaments present in the cells. Before making scanning electron micrograph pictures, cells are treated with $OsO_4$ and dried by critical point drying.

Details of the present invention can be provided by an image resulting from Scanning electron micrographs (SEM). The cell is primarily present on top of the array of microneedle bodies. At certain spots the neuron visibly engulfs the microneedles very tightly. The cell grows inside the access channel. A tight adhesion of the neuron cell to the microneedle can be demonstrated. This has been observed for different dimensions of microneedles, for different spacings between individual microneedles and for different diameters of the access channel.

Z-stacks of cells on microneedles with access channels 20 are made using confocal microscopy. It was observed that actin rings are present in the cell body around the outer part of the microneedles. Actin dots were observed coinciding with the access channels within the microneedles. This indicates that the cell cytoskeleton grows down into the access channel, and may grow down to the bottom level. It is not the cell as a whole but particularly actin filaments in the cytoskeleton. It is further observed on the images that the actin dots and the access channel 20 have the same diameter. This leads to the conclusion that the action filaments, e.g. the protruding portion of the cell, is adhered to the inner surface of the access channel 20.

Other Observations

The invention may be summarized as an electronic device for sensing and/or actuating comprising a device surface to which an biological cell is applied, further comprising a sensor and/or an actuator or other means for sensing and/or actuating, and an access channel with a channel port, said channel port being located in said surface. The access channel is designed such that the biological cell entering the access channel is provided access to the sensor. Suitably, the access channel has a longitudinal axis extending in a direction substantially perpendicular to a plane through said channel port. More suitably, the access channel has a restricted volume and an internal surface that is closed except for the channel port. In a preferred embodiment, a sensor or actuator is present at a sensor port within the access channel. The design of the access channel is particularly such that upon adhesion of the cell to the device surface within a cell adhesion area, a protruding portion is formed and enters into the access channel. It is the protruding portion that is thereafter sensed and/or actuated by the means thereto present in the access channel.

The invention disclosure further relates to the use of this device, in one of its various embodiments, particularly for sensing and/or actuating the protruding portion of a cell, particularly a neuron. Advantageously, it is used for enabling electroporation of the cell. The device may be further used for actuation of a biological cell as part of a cell stimulation treatment. The device could be further used for implantation into the human body. It may serve sensing or actuating purposes, but alternatively be used for the provision of a specific medicament to cells. The invention thus also relates to a method for the preparation of a medicine, particularly suitable for application to a cell in an electroporation process, wherein an active component is provided to the device of the invention. The active component is then stored in the access channel, for instance in a functionalized form attached to at least a portion of the inner surface.

It is observed for clarity that the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

The invention claimed is:

1. An electronic device comprising:
   a substrate with a device surface to which a biological cell can be applied; and
   one or more access channels provided on the substrate, wherein at least a single access channel of the one or more access channels has a longitudinal axis that extends in a direction substantially perpendicular to a plane through the substrate, the at least a single access channel comprising:
   (i) a channel port in the device surface at a top of the access channel,
   (ii) at least one sidewall extending from the channel port, wherein the at least one sidewall at least partially defines a restricted volume, and wherein an internal surface of the access channel is substantially closed except for the channel port,
   (iii) an electrode configured for actuating a protruding portion of the biological cell that enters the volume of the access channel, wherein the electrode extends along and covers the at least one sidewall; and
   (iv) a sensor configured to sense a property of the biological cell upon actuation of the protruding portion of the biological cell by the electrode, wherein the electrode and the sensor are distinct components of the electronic device, and wherein the sensor is disposed in the access channel, and is separated from the channel port by a space that extends along the longitudinal axis of the access channel.

2. The electronic device as claimed in claim 1, wherein the device surface has a non-planar shape with an extended surface area.

3. The electronic device as claimed in claim 1, comprising at least one microneedle on the substrate provided with the access channel, wherein the channel port is located at a tip of the microneedle.

4. The electronic device as claimed in claim 1, wherein the access channel further comprises a sensor port located adjacent a base of the access channel, wherein the base is at an end of the access channel that is opposite from the channel port, and wherein the sensor is located at the sensor port.

5. The electronic device as claimed in claim 4, wherein a surface portion of the device surface extending from the substrate is a microneedle, wherein the channel port is located at a tip of the microneedle.

6. The electronic device as claimed in claim 1, wherein the electrode is further configured for use as an electroporation element by applying voltage pulses to the protruding portion of the biological cell, and wherein the access channel further comprises a reagent suitable for interaction with at least the protruding portion of the biological cell.

7. The electronic device as claimed in claim 6, wherein the reagent is included in a self-assembled monolayer adhered to the inner surface of the access channel.

8. The electronic device as claimed in claim 1, wherein a ratio of a depth of the access channel to a diameter of the access channel is greater than five.

9. The electronic device as claimed in claim 1, wherein the sensor is at least one of a chemical sensor, a transistor-type sensor, or a capacitive sensor.

10. The electronic device as claimed in claim 1, wherein the internal surface of the access channel is hydrophilic.

11. The electronic device of claim 1, wherein the access channel comprises opposing sidewalls extending from the channel port, wherein the electrode extends continuously along and covers the opposing sidewalls to define the restricted volume therebetween.

12. The electronic device as claimed in claim 1, wherein in the at least a single access channel, the electrode is exposed to the internal surface of the access channel.

13. An electronic device comprising:
an electrode for actuating a biological cell and first and second microneedles provided on a substrate, each of the first and second microneedles comprising an access channel having a channel port located at a tip of the microneedle, wherein each access channel:
is designed to provide access to a biological cell applied at least one of (i) on the microneedle or (ii) around the microneedle,
has a longitudinal axis extending in a direction substantially perpendicular to a plane through the substrate,
has a depth-over-diameter ratio that is greater than five, and
defines a restricted volume configured to receive a portion of the biological cell, wherein an internal surface of the restricted volume is substantially closed except for the channel port,
wherein, the electrode extends continuously along the tip and inner surfaces of the access channels of the first and second microneedles.

14. The electronic device as claimed in claim 13, wherein, for each of the first and second microneedles, a diameter of the channel port is greater than a diameter of the access channel.

15. The electronic device as claimed in claim 13, wherein, for each of the first and second microneedles, the electrode covers substantially all of the internal surface of the restricted volume.

16. The electronic device as claimed in claim 13, wherein, for each of the first and second microneedles, the inner surface of the access channel is hydrophilic.

17. The electronic device of claim 13, wherein the internal surface of the restricted volume is closed except for the channel port.

18. A sensor device comprising:
at least two microneedles on a substrate, wherein each of the at least two microneedles comprises an access channel having a channel port, an electrode, and a sensor, wherein the electrode and the sensor are distinct components,
wherein, for each of the at least two microneedles, the access channel includes opposing sidewalls that define an inner surface of the access channel, and is designed for providing access to a biological cell that is at least one of (i) applied on the microneedle or (ii) applied around the microneedle,
wherein, for each of the at least two microneedles, the electrode is exposed to the inner surface of the access channel, and extends continuously along and between the opposing sidewalls of the access channel and defines a volume therebetween that is configured to receive at least a portion of the biological cell, wherein the electrode is configured for actuating the portion of the biological cell that enters the volume defined between the electrode extending along the opposing sidewalls,
wherein, for each of the at least two microneedles, the channel port is located at a tip of the microneedle, and
wherein, for each of the at least two microneedles, a ratio of a depth of the access channel to a diameter of the access channel is greater than five.

19. The electronic device as claimed in claim 18, wherein, for each of the at least two microneedles, an inner surface of the access channel is hydrophilic.

20. The electronic device as claimed in claim 18, wherein the sensor is disposed in the access channel, and is separated and spaced away from the channel port at the top of the microneedle.

* * * * *